(12) United States Patent
Van Es et al.

(10) Patent No.: US 7,810,187 B2
(45) Date of Patent: Oct. 12, 2010

(54) PATIENT HANDLING SYSTEM WHEREBY A PATIENT TABLE TOP CAN MOVE OVER A TABLE BASE

(75) Inventors: Arthur Robert Van Es, Eindhoven (NL); Ravindra Bhat, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 315 days.

(21) Appl. No.: 11/817,694

(22) PCT Filed: Mar. 7, 2006

(86) PCT No.: PCT/IB2006/050701

§ 371 (c)(1),
(2), (4) Date: Sep. 4, 2007

(87) PCT Pub. No.: WO2006/095308

PCT Pub. Date: Sep. 14, 2006

(65) Prior Publication Data

US 2008/0201849 A1    Aug. 28, 2008

(30) Foreign Application Priority Data

Mar. 9, 2005    (EP) .................................. 05101810

(51) Int. Cl.
*A61B 6/04* (2006.01)
*A61G 13/02* (2006.01)

(52) U.S. Cl. .......................................... 5/601; 378/209
(58) Field of Classification Search ..................... 5/601, 5/600; 378/209, 208
See application file for complete search history.

(56) References Cited

U.S. PATENT DOCUMENTS

| 4,131,802 | A | * | 12/1978 | Braden et al. | 5/601 |
| 4,545,571 | A | * | 10/1985 | Chambron | 5/601 |
| 4,568,071 | A | * | 2/1986 | Rice | 5/601 |
| 4,613,122 | A | | 9/1986 | Manabe | |
| 4,657,235 | A | * | 4/1987 | Schar | 5/611 |

(Continued)

FOREIGN PATENT DOCUMENTS

| EP | 562585 A2 | 9/1993 |
| EP | 757255 A2 | 11/2007 |

*Primary Examiner*—Robert G Santos

(57) ABSTRACT

A patient handling system comprising a table top (6) for carrying a lying patient (8). The table top (6) is supported by a table base (1) and the table top (6) can move in longitudinal direction over said table base (1) so that at least a part of the table top (6) can be displaced to a position away from said table base (1). At least a portion (1;4) of said table base (1), to which portion (1;4) the table top (6) is movably attached, can be displaced in substantially said longitudinal direction in which the table top (6) can move. Thereby, said table top (6) can be displaced in longitudinal direction over a distance which is larger than the length of the table top (6).

7 Claims, 2 Drawing Sheets

U.S. PATENT DOCUMENTS

| | | |
|---|---|---|
| 4,773,637 A | 9/1988 | Jarin |
| 5,039,867 A | 8/1991 | Nishihara et al. |
| 5,199,060 A * | 3/1993 | Kato .......................... 378/196 |
| 5,590,429 A * | 1/1997 | Boomgaarden et al. ........ 5/601 |
| 6,094,760 A | 8/2000 | Nonaka et al. |
| 6,615,428 B1 * | 9/2003 | Pattee ............................ 5/601 |
| 6,637,056 B1 * | 10/2003 | Tybinkowski et al. .......... 5/611 |
| 6,865,411 B2 * | 3/2005 | Erbel et al. ................. 600/407 |
| 6,955,464 B1 * | 10/2005 | Tybinkowski et al. ....... 378/209 |
| 7,043,784 B2 * | 5/2006 | Plannerer ....................... 5/601 |
| 7,065,813 B2 * | 6/2006 | Hoth et al. ..................... 5/601 |
| 7,167,739 B2 * | 1/2007 | Van De Rijdt et al. ...... 600/415 |
| 7,216,383 B2 * | 5/2007 | Heinl et al. .................... 5/601 |
| 7,357,575 B2 * | 4/2008 | Huber et al. ................. 378/209 |
| 2002/0104163 A1 | 8/2002 | Reimann |
| 2002/0120986 A1 | 9/2002 | Erbel et al. |
| 2003/0216637 A1 | 11/2003 | Ho et al. |
| 2004/0001571 A1 | 1/2004 | Jahrling |
| 2004/0261176 A1 * | 12/2004 | Plannerer ....................... 5/601 |
| 2004/0261177 A1 | 12/2004 | Hoth et al. |
| 2005/0060804 A1 * | 3/2005 | Heinl et al. .................... 5/601 |
| 2008/0098526 A1 * | 5/2008 | Doleschal et al. .............. 5/616 |
| 2008/0201849 A1 * | 8/2008 | Van Es et al. .................. 5/601 |

* cited by examiner

PATIENT HANDLING SYSTEM WHEREBY A PATIENT TABLE TOP CAN MOVE OVER A TABLE BASE

The invention is related to a patient handling system comprising a table top for carrying a lying patient, whereby the table top is supported by a table base and whereby the table top can move in longitudinal direction over said table base, so that at least a part of the table top can be displaced to a position away from said table base. The table top can be a rather stiff plate-like member, whereby the weight of a patient can be carried while it is supported by the table base only at one end of the table top. In another embodiment, a less stiff plate-like member can be used, whereby the table top is supported at more locations along the length of the table top. The table base is the supporting unit underneath the table top, which supporting unit is mounted on the floor of the room in which the patient handling system is installed. In general, the dimension of the table base in said longitudinal direction is less than the length of the table top.

Such medical patient handling system is disclosed in US-A-2004/0001571, which publication describes a system for medical emergency care comprising a relatively long movable table top, whereby the patient is lying on a radio transparent patient board, which patient board rests on the movable table top. The table top is supported by a stationary table base, whereby the table top can be moved in its longitudinal direction over the table base. Furthermore, the table top can be moved by the table base in vertical direction. The length of the table top is more than twice the length of the patient, and because of the limited dimensions of the table base, the patient can lie on the table top in such a way, that his complete body is away from the table base, i.e. there is no part of the table base below the patient. Therefore, all parts of the body of the patient can be surrounded by a digital imaging system like a CT scanner, so that a complete body scan can be made without displacing the patient with respect to the table top. In order to scan the complete body of the patient, the scanning device can move over the floor in said longitudinal direction with respect to the patient lying on the table top.

In general, a long table top for carrying a patient is a disadvantage. The medical examination and treatment devices have often large dimensions, and the available space to install these devices is mostly limited. Therefore, the dimensions of the patient handling system should be as small as possible, whereby, preferably, the length of the table top should not be much larger than the length of the patient. On the other hand, a position of the lying patient, whereby the complete body of the patient can be surrounded by a medical examination device such as a CT scanner is an advantage.

The object of the invention is an improved patient handling system comprising a table top for carrying a lying patient, whereby the table top is movably supported by a table base, whereby the table top has a limited length, and whereby the body of the patient lying on the table top can be brought in a position whereby it can be surrounded by a medical device such as a CT scanner or the like.

To accomplish with that object, at least a portion of said table base, to which portion the table top is movably attached, can be displaced in substantially said longitudinal direction in which the table top can move. Thereby, the table top with the patient lying on it can be displaced with respect to the table base to which it is connected over a certain distance and, furthermore, the table top can be additionally displaced by moving the table base, or by moving the portion of the table base to which the table top is attached. Thereby, the whole body of the patient can be moved, for example, in the examination space of a CT scanner, whereby the CT scanner is stationary mounted on the floor.

The invention can be applied in relation with any medical examination or treatment device. When hereinafter a CT scanner is mentioned is that only an example of the application of the invention.

In one preferred embodiment, said table top can be displaced in longitudinal direction over a distance which is larger than the length of the table top, while it is still connected to the table base. So, the table top can move between two positions, which two positions do not have a mutual overlap, i.e. there is a distance between the table top in one of the positions and the table top in the other position. Thereby, any part of the body of the patient can be placed in a stationary CT scanner, while the table top can also be brought completely outside the CT scanner in one operation.

Preferably, the table top is connected with the upper side of the table base by means of an interface member, which interface member is attached to the lower side of the table top near one end of the table top, and which interface member is movably attached to the upper side of the table base. Thereby, a maximal displacement of the table top can be achieved when the interface member can move over substantially the entire upper side of the table base, whereby a major part of the table top with the patient lying on it can extend away from the table base.

In one preferred embodiment, the upper side of the table base is provided with stationary supporting means for supporting the moving table top. Thereby, the upper side of the table base may comprise rollers or similar supporting means in order to support and guide the table top during its longitudinal sliding movement over the table base. Such supporting means may be present at different locations of the table base, whereby the table top is supported at these different locations, so that its position is more stable, whereby no large torque forces are applied on the table base and the table top.

Preferably, stationary supporting means for supporting the moving table top are present at a distance from the table base, in such a way that a medical device such as a CT scanner can be positioned between the table base and said stationary supporting means. Thereby, the table top can be supported at both sides of the medical device, so that its position is more stable.

In one preferred embodiment, said table base comprises a stationary portion that is fixed to the floor and a movable portion that can be displaced with respect to said stationary portion substantially in said longitudinal direction. The stationary portion can be firmly fixed to the floor of the room where the patient handling system is installed, while the movement of the movable portion of the table base increases the length of the path of movement of the table top. So, no further means than simple fixations means are required on the floor, because the means for additionally moving the table top are part of the table base.

In an other preferred embodiment, said table base is movably attached to the floor, whereby the table base can be displaced in substantially said longitudinal direction with respect to the floor. Thereby, guiding means on the floor of the room where the patient handling system is installed are required in order to move the table base. On the other hand, the table base itself can have a more simple and stable structure.

In one preferred embodiment, said table top is detachably connected with said table base, so that, for example, the table top can be taken over by a trolley. Thereby, there is no need to move the patient from one patient support table to an other support table, because he can stay on the same patient support table top during his transport and his treatment and/or examination. Thereby, preferably, the table top is connected with the upper side of the table base by means of an interface member, which interface member is detachably attached to the lower side of the table top near one end of the table top, and which interface member is movably attached to the upper side of the table base.

The invention will now be further elucidated by means of a description of two embodiments of a patient handling system comprising a table top for carrying a lying patient and a table base for supporting the table top, and whereby the table top can move in longitudinal direction over said table base, whereby reference is made to the drawing comprising Figures which are only diagrammatical representations of the system, in which.

Figure 1:
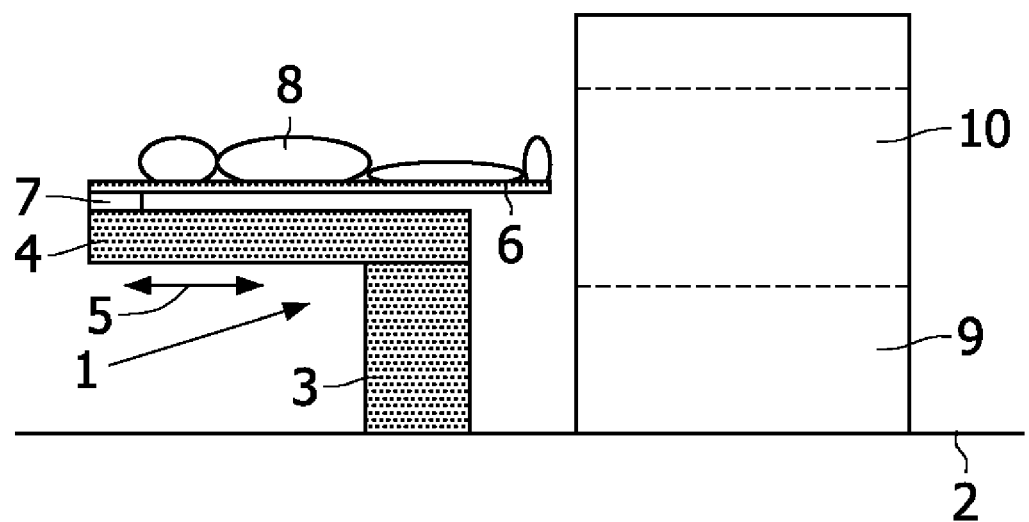
FIG. 1 shows a first embodiment with the table top above the table base.

FIG. 1 shows schematically a table base 1 mounted at a fixed position on the floor 2 of the room in which the patient handling system is installed. The table base comprises a stationary portion 3 and a movable portion 4. The movable portion 4 can move in horizontal direction with respect to the stationary portion 3, as is indicated with arrow 5. Above the table base 1 is a table top 6 extending in horizontal direction, which table top 6 is connected with portion 4 of the table base 1 by means of an intermediate interface member 7. Interface member 7 is attached to the lower side of the table top 6 near the end of it at a fixed location. The lower side of the interface member 7 is attached to portion 4 of the table base 1, whereby the interface member 7 can slide over portion 4 of the table base 1 by means of a rail structure (not shown in the Figure). The table top 6 is carrying a patient 8 and it is stable and solid (stiff), so that the interface member 7 at one end of the table top 6 provides for an appropriate support for the table top 6 and the patient 8.

Furthermore, FIG. 1 shows a medical CT scanner 9 comprising a substantial cylindrical scanning space 10. The portion of the patient 8 that is located in the center of the scanning space 10 can be scanned by the CT scanner (see FIG. 2).

Figure 2:
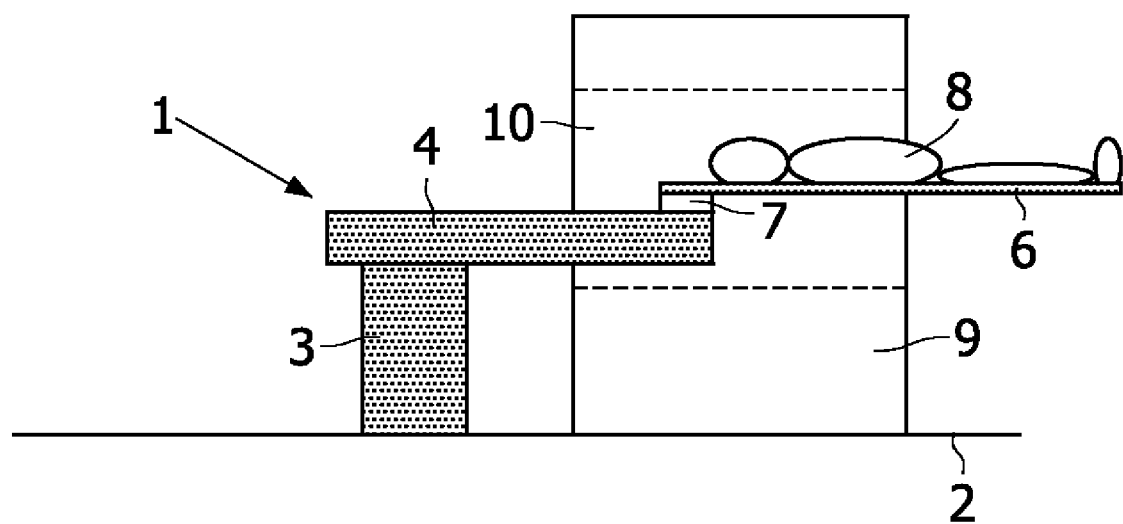
FIG. 2 shows the first embodiment with the table top in a CT scanner.

FIG. 2 shows that the patient 8 is moved into the cylindrical scanning space 10 of the CT scanner 9. Thereby, the movable portion 4 of the table base 1 is displaced to the right (in the Figure) with respect to the stationary portion 3, and furthermore, the interface member 7 is moved to the right with respect to the movable portion 4 of the table base 1. Because of the two movements (double stroke) to the right, the table top 6 can be moved from a position completely outside the CT scanner 9 (FIG. 1) to positions whereby each part of the table top 6 is present in the center of the scanning space 10 of the CT scanner 9. Therefore a complete body-scan of the patient 8 can be made without displacing the patient 8 on his supporting carrier (table top 6).

Figure 3:
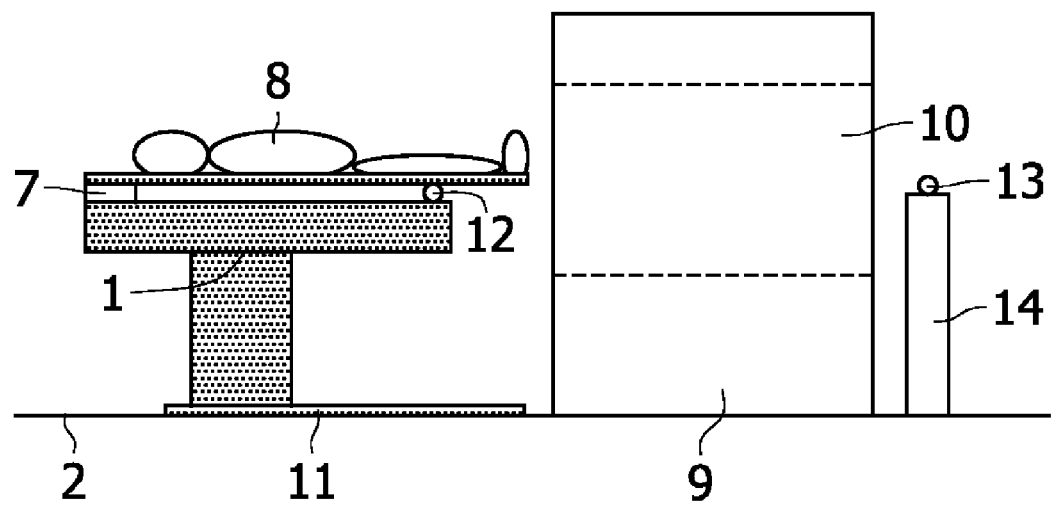
FIG. 3 shows a second embodiment with the table top above the table base.
Figure 4:
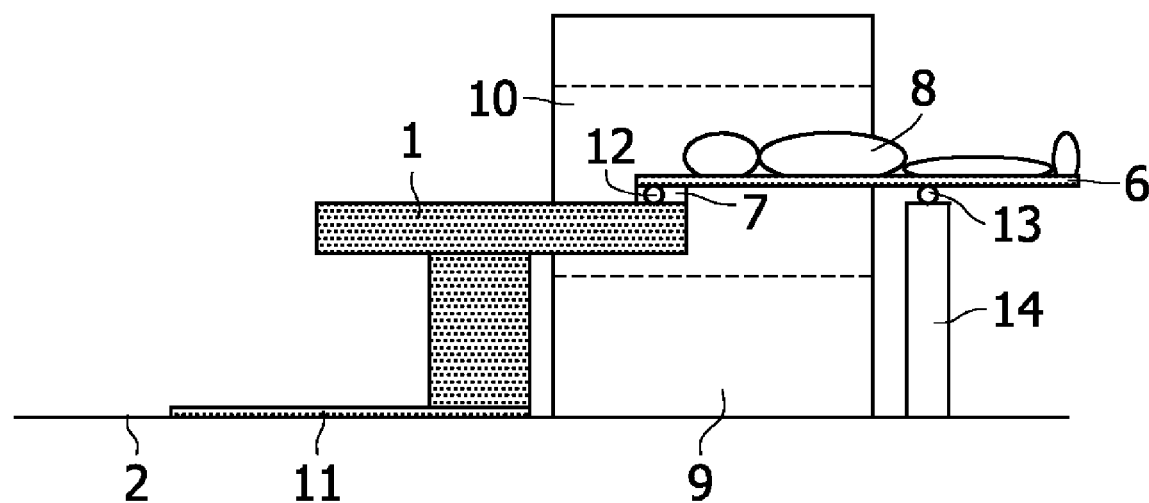
FIG. 4 shows the second embodiment with the table top in a CT scanner.

FIGS. 3 and 4 show schematically the second embodiment of the patient handling system, whereby similar parts are indicated with the same reference numerals as in the FIGS. 1 and 2 showing the first embodiment. According to the second embodiment the table base 1 does not have a stationary portion and a movable portion, but the whole table base 1 is movable along a rail 11 on the floor 2.

Just like in the first embodiment, an interface member 7 is movably attached to the upper side of the table base 1, as is shown in FIG. 3. The upper side of the interface member 7 is attached to the lower side of the table top 6 near the end of the table top 6 at a fixed location. The table top 6 is not only supported by the interface member 7, but also by two rollers 12, which two rollers 12 are mounted at the upper side of the table base 1. The two rollers 12 engage the lower side of the table top 6 near both longitudinal edges of it.

In FIG. 3 the complete table top 6 is positioned outside the CT scanner 9, so that the patient 8 can be easily placed on the table top 6. As a preferred alternative, the table top 6 is detachably connected to the interface member 7, so that it can be taken over by a trolley, as it is, for example, described in US-A-2004/0001571, mentioned before.

In order to move the patient 8 into the scanning space 10 of the CT scanner 9, the table base 1 is moved to the right (FIG. 4) over the floor 2, and subsequently, the table top 6 is moved to the right with respect to the table base 1. Thereby, the support of the table top 6 is partly taken over by the two rollers 13 attached to the upper side of support device 14 at the other side of the CT scanner 9. The two rollers 13 engage the table top 6 at its lower side near its longitudinal edges, just like the two rollers 12. In the position of the table top 6 as represented in FIG. 4, the interface member 7 is located between the two rollers 12. Due to the additional support of the rollers 12,13, the table top 6 can be made less stiff and simpler.

The two embodiments as described above are merely examples of the patient handling system according to the invention; a great many other embodiments are possible. In particular, as an example of a further preferred embodiment, the patient handling system according the described first embodiment may have the supporting rollers 12,13 as present in the described second embodiment.

The invention claimed is:

1. A patient handling system comprising a table top for carrying a lying patient, whereby the table top is supported by a table base and whereby the table top can move in a longitudinal direction over said table base so that at least a part of the table top can be displaced to a position away from said table base, wherein at least a portion of said table base, to which portion the table top is movably attached, can be displaced in substantially said longitudinal direction in which the table top can move, and wherein the table top is detachably connected with the upper side of the table base by means of an interface member to enable a patient to stay on a same table top during transport, treatment, and/or examination without needing to move the patient from one table top to another table top, further wherein the interface member is (i) detachably attached to the lower side of the table top near only one end of the table top, and (ii) movably attached to the upper side of the table base, the interface member further being configured to move over the entire upper side of the table base to enable a maximal displacement and an extending away of a major part of the table top from the table base via the interface member near only one end of the table top in order to allow the whole body of the patient to be transported, treated, and/or examined without displacing the patient with respect to the table top.

2. A patient handling system as claimed in claim 1, wherein said table top can be displaced in a longitudinal direction over a distance which is larger than the length of the table top.

3. A patient handling system as claimed in claim 1, wherein the upper side of the table base is provided with stationary supporting means for supporting the moving table top.

4. A patient handling system as claimed in claim 1, wherein stationary supporting means for supporting the moving table top are present at a distance from the table base.

5. A patient handling system as claimed in claim 1, wherein said table base comprises a stationary portion that is fixed to the floor and a movable portion that can be displaced with respect to said stationary portion substantially in said longitudinal direction.

6. A patient handling system as claimed in claim 1, wherein said table base is movably attached to the floor, whereby the table base can be displaced in substantially said longitudinal direction with respect to the floor.

7. A patient handling system comprising a table top for carrying a lying patient, whereby the table top is supported by a table base and whereby the table top can move in a longitudinal direction over said table base so that at least a part of the table top can be displaced to a position away from said table base, wherein at least a portion of said table base, to which portion the table top is movably attached, can be displaced in substantially said longitudinal direction in which the table top can move, and wherein the table top is detachably connected with the upper side of the table base by means of an interface member to enable a patient to stay on a same table top during transport, treatment, and/or examination without needing to move the patient from one table top to another table top, further wherein the interface member is (a)(i) detachably attached to the lower side of the table top near only one end of the table top, and (a)(ii) movably attached to the upper side of the table base, the interface member further being configured to move over the entire upper side of the table base to enable a maximal displacement and an extending away of a major part of the table top from the table base via the interface member near only one end of the table top in order to allow the whole body of the patient to be transported, treated, and/or examined without displacing the patient with respect to the table top, further wherein the upper side of the table base is provided with stationary supporting means for supporting the moving table top, the stationary supporting means including two rollers mounted to the upper side of the table base and configured to engage the lower side of the table top near both longitudinal edges of the table top, and wherein (b)(i) for a first position of the table top, the interface member is located at an opposite end of upper side of the table base from the two rollers and (b)(ii) for a maximal displacement position of the table top, the interface member is located at the upper side of the table base between the two rollers.

* * * * *